US011234661B2

(12) United States Patent
Dirisio

(10) Patent No.: US 11,234,661 B2
(45) Date of Patent: *Feb. 1, 2022

(54) MAGNETIC BRAKING SYSTEM AND METHOD

(71) Applicant: CARESTREAM HEALTH, INC., Rochester, NY (US)

(72) Inventor: Anthony Dirisio, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 138 days.

This patent is subject to a terminal disclaimer.

(21) Appl. No.: 16/683,599

(22) Filed: Nov. 14, 2019

(65) Prior Publication Data
US 2020/0155083 A1 May 21, 2020

Related U.S. Application Data

(60) Provisional application No. 62/769,055, filed on Nov. 19, 2018.

(51) Int. Cl.
*H05G 1/02* (2006.01)
*A61B 6/10* (2006.01)
(Continued)

(52) U.S. Cl.
CPC ............ *A61B 6/105* (2013.01); *A61B 6/4405* (2013.01); *A61B 6/4458* (2013.01); *F16D 55/02* (2013.01);
(Continued)

(58) Field of Classification Search
CPC ..... A61B 6/105; A61B 6/4405; A61B 6/4452; A61B 6/4458; A61B 6/4476; A61B 6/447; A61B 6/4482; A61B 6/025; A61B 6/032; A61B 6/035; A61B 6/0442; A61B 6/0487; A61B 6/4007; A61B 6/4085; A61B 6/4266; A61B 6/4275; A61B 6/4435; A61B 6/4447; A61B 6/501; A61B 6/10; A61B 6/4464; A61B 6/00; A61B 6/0414; A61B 6/467; A61B 6/548; A61B 50/10; A61B 6/0407; A61B 6/06; A61B 6/08; A61B 6/4283; A61B 6/4441; A61B 6/588; A61B 6/04; A61B 6/5276; A61B 34/30; A61B 2090/508; A61B 90/50; A61B 34/76; A61B 34/37; A61B 2017/00212; A61B 2090/506; A61B 34/25; A61B 34/35; A61B 34/74; A61B 90/37; A61B 2090/571;
(Continued)

(56) References Cited

U.S. PATENT DOCUMENTS 3,609,355 A * 9/1971 Schwarzer ............. A61B 6/502
378/37
3,655,967 A * 4/1972 Finkenzeller .......... A61B 6/145
378/196

(Continued)

*Primary Examiner* — Irakli Kiknadze

(57) ABSTRACT

A mobile radiography system includes a wheeled transport frame and a vertical column mounted on the transport frame. A telescoping arm is attached to the vertical column and to an x-ray tube head. The telescoping arm allows an operator to rotate the tube head to a desired orientation and then to fix the tube head in the desired orientation without mechanical impact noise. A permanent magnet and an electromagnetic coil assembly allows an operator to easily and quietly control rotation of the tube head.

12 Claims, 7 Drawing Sheets

(51) Int. Cl.
  *F16D 55/02* (2006.01)
  *A61B 6/00* (2006.01)
  *F16D 65/18* (2006.01)
  *F16D 121/20* (2012.01)
  *G03B 42/02* (2021.01)

(52) U.S. Cl.
  CPC ........ *F16D 65/186* (2013.01); *F16D 2121/20* (2013.01); *G03B 42/02* (2013.01); *H05G 1/02* (2013.01)

(58) Field of Classification Search
  CPC .. F16D 2121/20; F16D 2121/22; F16D 55/02; F16D 59/02; F16D 63/008; F16D 65/186; F16D 2121/18; F16D 69/02; G03B 42/02; H05G 1/02; H05G 1/025; H05G 1/60; H05G 1/64; G01N 2223/301; G01N 2223/308; G01N 23/04; G01N 23/083; G01N 23/087; G01N 2333/4748; G01N 2500/00; G01N 33/5748; G01N 33/6848; G01N 23/043; F04C 2270/041; F16C 17/10; F16C 2316/10; A61N 5/1081; A61N 5/1049; A61N 2005/1061; A61N 2005/1087; A61N 5/1048; A61N 5/107; A61G 13/04; A61G 13/06; A61G 13/104; A61G 2203/12; A61G 2203/14; A61G 2203/20; A61G 2203/42; A61G 2210/50; A61G 2203/10; A61G 2203/32; A61G 2203/40; A61G 2203/44; A61K 2300/00; A61K 31/138; A61K 31/185; A61K 31/194; A61K 31/285; A61K 31/29; A61K 31/65; A61K 31/704; A61K 31/7048; A61K 31/706; A61K 31/7068; A61K 33/24; A61K 33/243; A61K 33/245; A61K 33/36; A61K 38/00; A61K 45/06; A61K 9/0014; A61K 9/0019; A61K 9/0043; H02K 49/10
  USPC .................................................. 378/197, 198
  See application file for complete search history.

(56) References Cited

U.S. PATENT DOCUMENTS

| | | |
|---|---|---|
| 4,964,152 A | 10/1990 | Kaul et al. |
| 8,465,203 B2 | 6/2013 | Barker et al. |
| 8,876,379 B2 | 11/2014 | DiRisio et al. |
| 2003/0217901 A1 | 11/2003 | Carlson |
| 2011/0249806 A1* | 10/2011 | Wendlandt ........... A61B 6/4482 378/198 |
| 2013/0077765 A1* | 3/2013 | Welsh .................... A61B 6/588 378/198 |
| 2016/0069439 A1 | 3/2016 | Davies |
| 2018/0353055 A1* | 12/2018 | Geiger ................. A61B 1/0016 |
| 2020/0155083 A1 | 5/2020 | DiRisio |
| 2020/0155090 A1 | 5/2020 | DiRisio |
| 2020/0155091 A1 | 5/2020 | DiRisio |

\* cited by examiner

MAGNETIC BRAKING SYSTEM AND METHOD

CROSS REFERENCE TO RELATED APPLICATIONS

This application claims priority to U.S. patent application Ser. No. 62/769,055, filed Nov. 19, 2018, in the name of Dirisio et al., and entitled BRAKING SYSTEM AND METHOD, which is hereby incorporated by reference herein in its entirety.

This application is related in certain respects to U.S. Pat. No. 8,876,379 B2, filed Apr. 11, 2011, in the name of Dirisio et al., and entitled COLLAPSIBLE COLUMN MOVEMENT APPARATUS FOR MOBILE X-RAY DEVICE, which is hereby incorporated by reference herein in its entirety.

BACKGROUND OF THE INVENTION

The invention relates generally to the field of medical imaging, and in particular to portable radiographic imaging apparatus. More specifically, the invention relates to a mobile radiography apparatus including improved operational features.

Mobile carts are employed in medical facilities to move medical equipment between locations. One type of mobile cart includes an x-ray source used to capture digital x-ray images in a digital radiographic detector. Mobile x-ray apparatus are of particular value in intensive care apparatus (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

The discussion above is merely provided for general background information and is not intended to be used as an aid in determining the scope of the claimed subject matter.

BRIEF DESCRIPTION OF THE INVENTION

A mobile radiography system includes a wheeled transport frame and a vertical column mounted on the transport frame. A telescoping arm is attached to the vertical column and to an x-ray tube head. The telescoping arm allows an operator to rotate the tube head to a desired orientation and then to fix the tube head in the desired orientation without mechanical impact noise. A permanent magnet and an electromagnetic coil assembly allows an operator to easily and quietly control rotation of the tube head.

In one embodiment, a mobile radiography system includes a transport frame having wheels attached thereto for rollably transporting the system. A vertical column is mounted on the transport frame, a horizontal boom is attached to the vertical column, and an x-ray tube head is attached to the horizontal boom. A rotation assembly is attached to the horizontal boom and to the tube head. The rotation assembly includes a non-rotating rotor and a mount for attaching a tube head thereto. The mount is attached to a rotatable shaft. The mount includes a brake pad configured to press against the rotor using a permanent magnet, and an electromagnetic coil is configured to counteract the permanent magnet when the electromagnetic coil is activated.

In another embodiment, a brake assembly includes a rotor and a brake mechanism configured to rotate relative to the rotor when the brake mechanism is deactivated. A pressure source in the brake mechanism presses a brake pad against the rotor. An electrically powered assembly deactivates the brake mechanism when power is provided to the electrically powered assembly.

In another embodiment, a radiography system includes an x-ray source and an arm mechanically supporting the x-ray source. The arm allows rotating the x-ray source using a rotation assembly which includes a rotationally stationary rotor in the shape of a ring, and a brake mechanism having a brake pad. The brake mechanism rotates along a path on the rotor when the brake mechanism is deactivated. The brake mechanism presses the brake pad against the rotor to prevent rotation of the brake mechanism when the brake mechanism is not deactivated.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
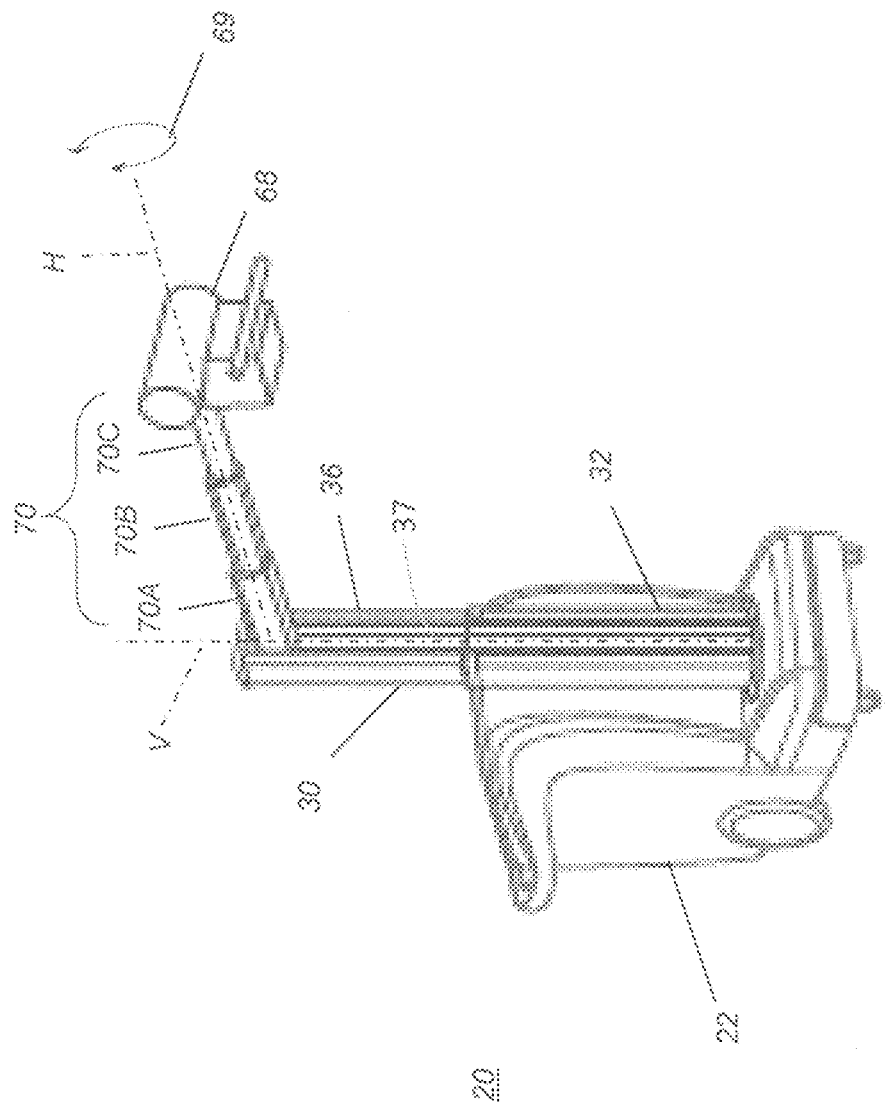
FIG. 1 is a perspective view of a mobile radiography apparatus.

With reference to FIG. 1 a mobile radiography apparatus 20 includes a telescoping boom 70 coupled to a telescoping, sectioned vertical column 30 according to one embodiment. An x-ray tube head 68 is in position for imaging, extended from vertical column 30, and supported, by boom 70 along a horizontal axis H that may be perpendicular, or slightly angled, relative to the vertical axis V. The mobile radiography apparatus 20 has a wheeled transport frame 22. Telescoping sectioned vertical column 30 is mounted on frame 22 parallel to the vertical axis V and has a vertically stationary base section 32 that seats against the frame 22. At least one movable section 36 of the vertical column 30 is vertically translatable within the stationary base section 32 to extend along the vertical axis V, so that boom 70 and x-ray tube head 68 can be set to a suitable height over a range of possible height settings. Boom 70 includes three tubular boom sections 70A, 70B, 70C, each having a relatively decreasing cross sectional area, respectively. The boom section 70C, having the smallest cross sectional area, is rotatably attached to the x-ray tube head 68, to allow the tube head 68 to rotate about axis H, as indicated by double headed arrow 69. Boom section 70A, having the largest cross sectional area, is attached to the vertical column 30 by boom support frame 40 (FIG. 3) to allow height adjustment of the boom 70 along a vertical track 37 in the vertical column 30. Boom section 70A is not horizontally adjustable so that it remains in a fixed horizontal position relative to column 30. Boom section 70B is movable relative to boom section 70A by sliding into or out of boom section 70A parallel to horizontal axis H. Boom section 70C is movable relative to boom section 70A and boom section 70B by sliding into or out of boom section 70B parallel to horizontal axis H.

Figure 2B:
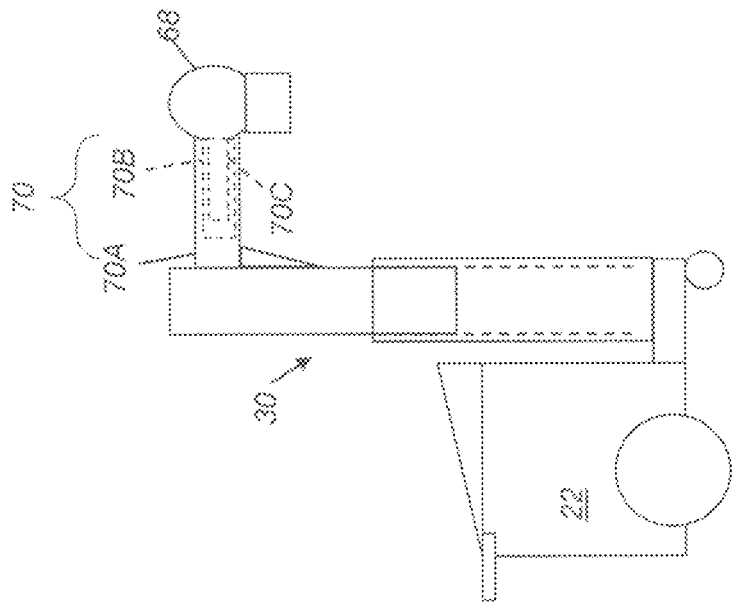
FIGS. 2A-2D are schematic side views of the mobile radiography apparatus of FIG. 1.
Figure 2A:
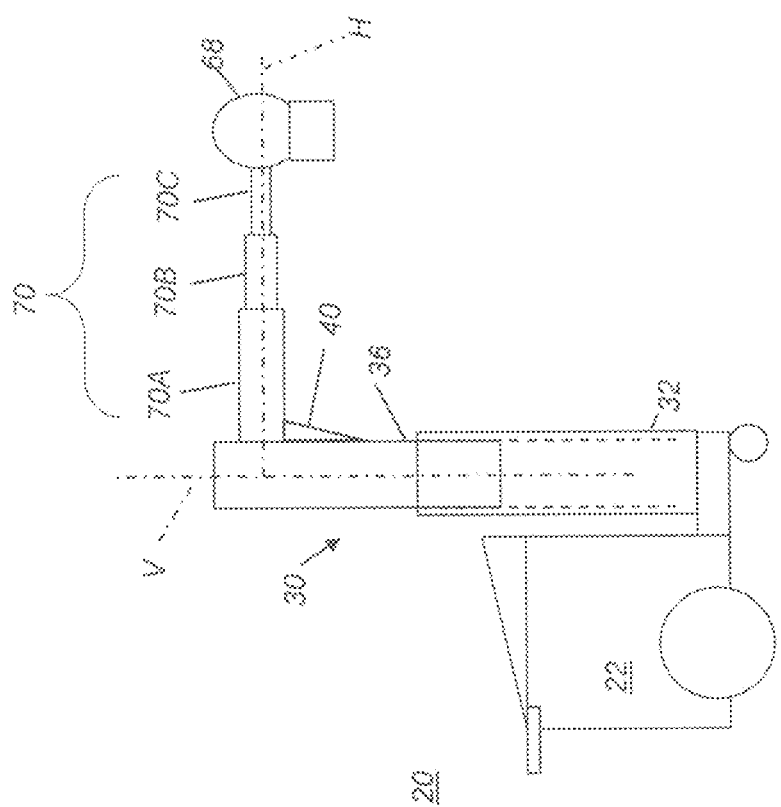
Figure 2C:
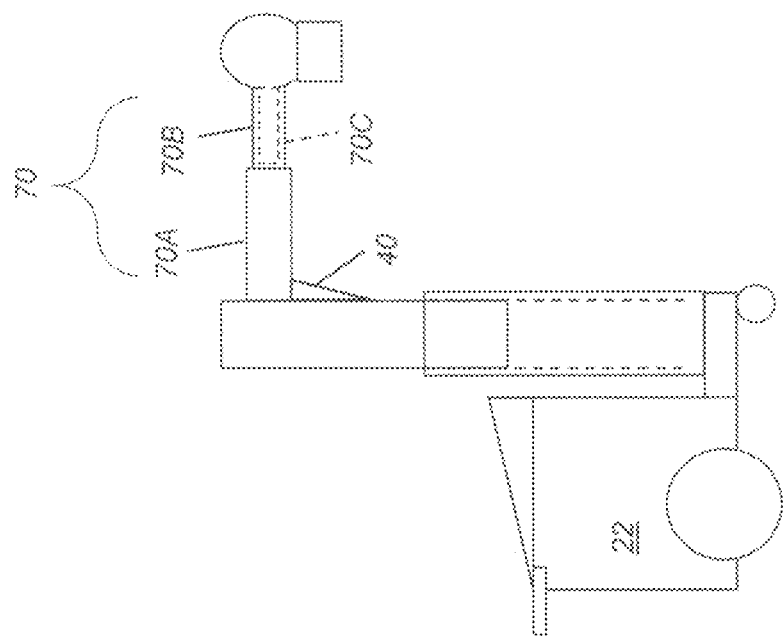
Figure 2D:
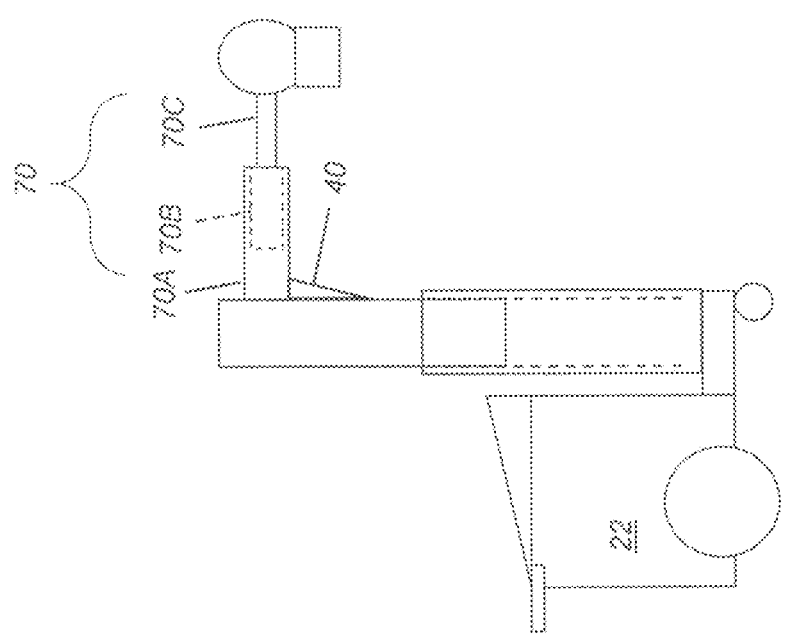

Embodiments of the present invention use a boom brake assembly (FIG. 4) that cooperates mechanically within the telescoping boom 70 to allow horizontal displacement of the x-ray tube head 68 over a wide range of horizontal positions as described herein. An operator can easily adjust a height of the boom 70 along vertical column 30 and a horizontal distance of the x-ray tube head 68 from the vertical column 30. As shown in FIG. 2A, stationary base section 32 may include a hollow cavity or shaft allowing movable section 36 to travel vertically therethrough. The boom 70 may be raised to a height near the top of movable section 36 while movable section 36 is extended vertically within the shaft of stationary base section 32. As shown in FIG. 2B, the boom 70 may be collapsed to its shortest length by manually urging the tube head 68 toward the vertical column 30 so that boom section 70B slides into boom section 70A and boom section 70C slides into boom section 70B. FIG. 2C-2D illustrate optional movement capabilities of the boom sections 70B, 70C. In FIG. 2C, boom section 70B is fully inserted into boom section 70A while boom section 70C is not inserted into boom section 70B. In FIG. 2D, boom section 70C is fully inserted into boom section 70B while boom section 70B is not inserted into boom section 70A. Thus, the boom sections 70B, 70C, may each be fully or partially manually inserted by sliding one or both of them into the corresponding larger boom section, as desired.

Figure 3:
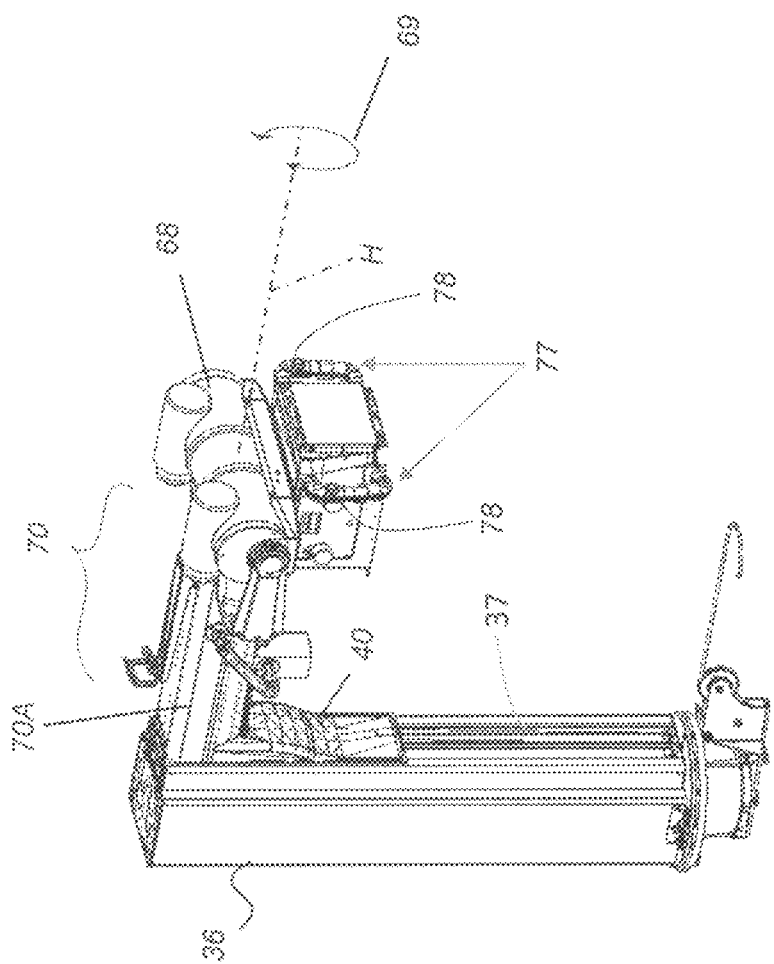
FIG. 3 is a partial perspective view of the schematic view of FIG. 2B.

FIG. 3 shows the movable upper section 36 in isolation together with boom 70 in a fully collapsed position having boom sections 70B and 70C within boom section 70A, corresponding to the same position as in FIG. 2B, x-ray tube head 68, and the boom support frame 40 that is secured to boom section 70A and to a track 37 used to raise and lower the boom 70 and x-ray tube head 68. X-ray tube head 68 may be rotated about the horizontal axis H in clockwise or counterclockwise directions 69. Handles 77 are attached to the tube head 68 to allow an operator to manually adjust a height of the tube head 68, to extend and retract the tube head away and toward the vertical column 30 by operation of the boom 70 as described herein, and to rotate the tube head 68 about a horizontal axis H. Control switches 78 are positioned, one on each of the handles 77, for controlling rotational movement of the x-ray tube head 68, as described hereinbelow.

Applicants have noted that during the operation of rotating the tube head 68 there can be an improvement in the operation. For example, reducing noise, so as to not interfere or adversely affect the comfort of the patient and medical technician or improving smoothness of the operation so as to improve the usability and ease of comfort of the medical technician. Applicants have developed a brake assembly to improve the operation of the mobile radiography apparatus 20. One benefit is to eliminate/reduce noise which may occur during rotation of the tube head 68. The tube head 68 and the components employed to rotate the tube head 68 have many contact points that slide against and contact each other during rotation. Applicants' brake assembly, as described herein, mitigates undesirable noise issues.

Figure 4:
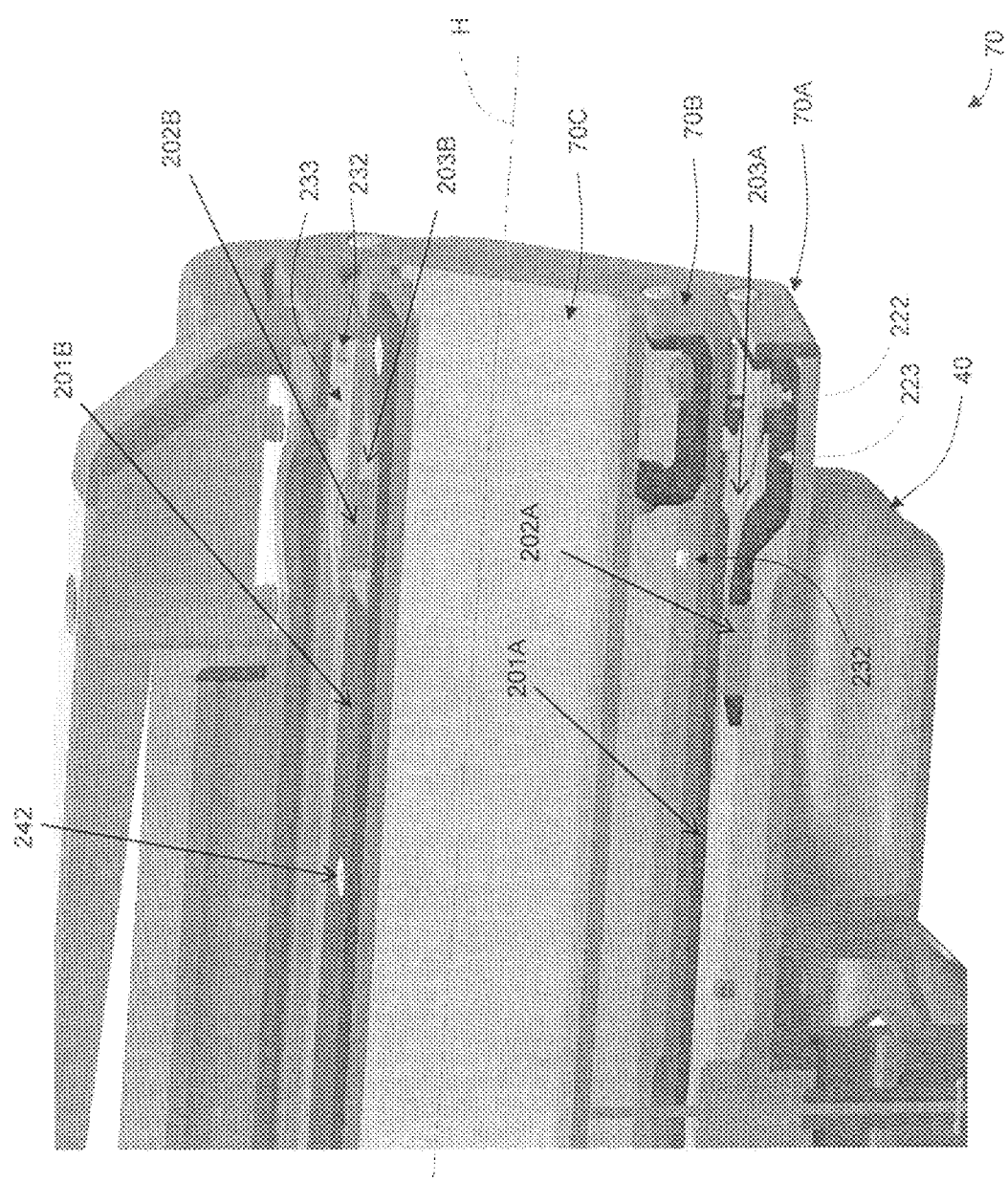
FIG. 4 is cross section view of an end portion of the boom.

FIG. 4 illustrates a cross section of boom 70 at a terminal end thereof where the tube head 68 is attached. The boom 70 includes a polymer magnetic brake assembly including brake plates 201A, 201B, magnets 202A, 202B, and polymer friction material 203A, 203B. The brake plate 201A, magnet 202A, and polymer friction material 203A may be considered as part of boom section 70A used to control sliding movement of boom section 70B therewithin, parallel to horizontal axis H. The brake plate 201B, magnet 202B, and polymer friction material 203B may be considered as part of boom section 70B used to control sliding movement of boom section 70C therewithin, parallel to horizontal axis H. In one embodiment, the magnets 202A, 202B, may be made from neodymium, an alloy of neodymium, iron and boron (NdFeB), and the polymer material 203A, 203B, may be made from Ultra High Molecular Weight Polyethylene (UHMWPE). Typical brake assemblies suffer from frictional material wear which causes changes in frictional force over time. The frictional wear may also create dust and debris. UHMWPE was selected for a friction material because of its low coefficient of friction and its superior wear properties. The coefficient of friction provided by the polymer material 203A, 203B, may require a normal force provided by the magnets 202A, 202B, to hold the polymer material 203A, 203B, against the brake plates 201A, 201B. There are no moving parts or adjustments required in this type of brake assembly.

As shown in the example embodiment of FIG. 4, the boom 70 includes a linearly extendable and retractable tubular design as shown. A boom support frame 40 may be used to support the boom 70 in a substantially horizontal position. The boom 70 includes tubular sections 70A, 70B, 70C. Tubular section 70A may be a stationary section with respect to boom support frame 40, being fixably secured thereto. Tubular section 70B may be configured to travel parallel to longitudinal axis H by sliding within tubular stationary section 70A and relative to tubular section 70C. Tubular section 70B may have a brake plate 201A secured thereto using one or more screws 232 along its length. Stationary section 70A may include a bracket 223 secured thereto which includes a cutout portion to hold magnet 202A in position to prevent the magnet 202A from traveling with section 70B when section 70B moves parallel to longitudinal axis H. Frictional material 203A is positioned between magnet 202A and brake plate 201A and is secured in place by a fastener 222 secured to the frictional material 203A and to bracket 223. Brake plate 201A is made from a material to which magnet 202A is attracted. Magnet 202A is free to move in a direction normal to brake plate 201A and is separated therefrom by a thickness of frictional material 203A, thereby pressing the frictional material 203A against brake plate 201A to provide a constant drag force against movement of section 70B relative to stationary section 70A. The drag force provided is not sufficient to prevent sliding movement of section 70B relative to stationary section 70A, such as by an operator's manual urging thereof, but may be sufficient to hold section 70B in place relative to section 70A to prevent unintended movement caused by, for example, gravitational force, vibrations or bumping.

Tubular section 70C may be configured to travel parallel to longitudinal axis H by sliding within tubular section 70B and relative to stationary tubular section 70A. Tubular section 70C may have a brake plate 201B secured thereto using one or more screws 242 along its length. Tubular section 70B may include a bracket 233 secured thereto which includes a cutout portion to hold magnet 202B in position to prevent the magnet 202B from traveling with section 70C when section 70C moves parallel to longitudinal axis H. Frictional material 203B is positioned between magnet 202B and brake plate 201B and is secured in place by a fastener 232 secured to the frictional material 203B and to bracket 233. Brake plate 201B is made from a material to which magnet 202B is attracted. Magnet 202B is free to move in a direction normal to brake plate 201B and is separated therefrom by a thickness of frictional material 203B, thereby pressing the frictional material 203B against brake plate 201B to provide a constant drag force against movement of section 70C relative to section 70B. The drag force provided is not sufficient to prevent sliding movement of section 70C relative to section 70B, such as by an operator's manual urging thereof, but may be sufficient to hold section 70C in place relative to section 70B to prevent unintended movement caused by, for example, gravitational force, vibrations or bumping.

Figure 5:
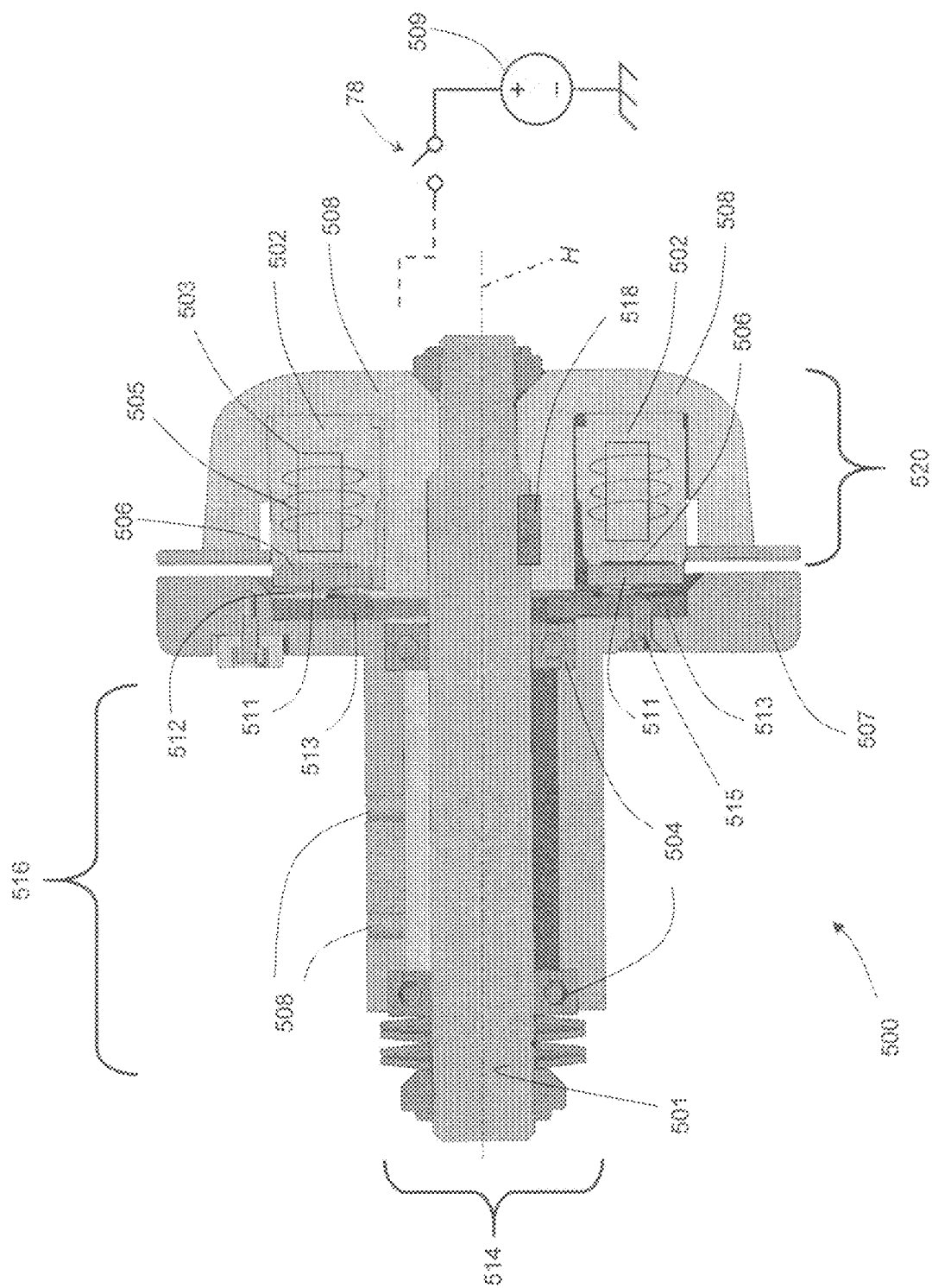
FIG. 5 is a cross section view of the rotation assembly for attaching the tube head to the end portion of the boom.

With reference to FIG. 5, there is illustrated a rotation assembly 500 for rotatably attaching the x-ray tube head 68 to the boom 70 to allow the tube head 68 to rotate about axis H, as indicated by double headed arrow 69 in FIGS. 1, 3. Rotation assembly 500 is a circular assembly, when viewed from the right or left in the perspective of FIG. 5, and includes stationary insertion section 516, having a width 514, that fits into boom section 70C (FIG. 4) by insertion therein. Screws (not shown) disposed through screw holes in boom section 70C may be threaded into screw holes 508 in the insertion section 516 to secure the rotation assembly 500 to boom section 70C of the boom 70. The shaft 501 rotates freely within stationary insertion section 516 using bearing assemblies 504 attached to the insertion section 516. Rotation assembly 500 includes rotatable section 520 having a mount 508 to which the x-ray tube head 68 may be attached by suitable mechanical means such as screws and/or clamps, for example. The mount 508 is fixably secured to the shaft 501 using a key 518, for example, and rotates together with the shaft 501. Attached to the mount 508 are coil and permanent magnet assemblies 502, each including a permanent magnet 503 such as a neodymium magnet, an electrically conductive electromagnetic coil 505, and a thin frictional material, or brake pad, 506. The coil and permanent magnet assemblies 502 rotate together with the mount 508 and the shaft 501. Rotation of the coil and permanent magnet assemblies 502, the mount 508 and the shaft 501 is typically in response to urging by an operator of the mobile radiography apparatus 20 who, such as by grasping the handles 77 (FIG. 3) of the x-ray tube head 68, rotates the x-ray tube head 68 to a desired position during a radiographic imaging exam.

Stationary insertion section 516 includes a flange portion 507 attached to bidirectional flexure plate 600 (FIG. 6) using screws 515 through the flange portion 507. The bidirectional flexure plate, which may be referred to herein as a rotor, includes two metal rings 511, 513, and a thin sheet metal ring 512 secured therebetween. The metal ring 513 of the bidirectional flexure plate is secured to the flange portion 507 using the screws 515. The bidirectional flexure plate 600 remains stationary together with the insertion section 516. Attachment of the shaft 501 to the stationary insertion section 516 and to the mount 508 is measured such that the friction material, or brake pad, 506 of each of the coil and permanent magnet assemblies 502 makes contact with the metal ring 511 of the flexure plate 600. As the coil and permanent magnet assemblies 502, the mount 508 and the shaft 501 are rotated by an operator as described herein below, the friction material 506 lightly contacts, as opposed to being pressed against, a surface of the metal ring 511 that faces the coil and permanent magnet assemblies 502 along a circular path on the metal ring 511. The permanent magnet 503 in each coil and permanent magnet assembly 502 is configured to attract and press the metal ring 511 tightly against the friction material 506 so as to prevent unintentional rotation of the mount, i.e., unintentional rotation of the x-ray tube head 68 attached thereto, caused by, for example, gravitational force, vibrations or bumping, by providing a sufficient frictional resistance against such rotation. Such frictional resistance serves to maintain a desired angular orientation of the x-ray tube head 68 as positioned by an operator of the mobile radiography apparatus 20. The electrically conductive coil 505 in each coil and permanent magnet assembly 502 is configured to generate an electromagnetic field, when activated, that is sufficiently strong to counteract the magnetic field of the permanent magnet 503. When the electrically conductive coil 505 is thus activated the frictional resistance provided by the permanent magnet 503 pressing the friction material 506 against the metal plate 511 is negated and the mount 508, as well as the x-ray tube head 68 attached thereto, is released to freely rotate about the horizontal axis H. An operator may activate the electrically conductive coil 505 using either of the control switches 78 on the handles 77 of the x-ray tube head 68 (FIG. 3). A power source 509 is electrically connected to both of the electrically conductive coils 505 in the coil and permanent magnet assemblies 502 to activate the electrically conductive coils 505 when either of the control switches 78 are switched by an operator. One or both of the switches 78 may be configured to connect power source 509 to the electromagnetic coils 505 when one or both of the switches 78 are depressed and to disconnect power source 509 from the electromagnetic coils 505 when one or both of the switches 78 are released. Thus, in a typical procedure for positioning the x-ray tube head 68, an operator may grasp the handles 77; then manually depress either or both the control switches 78 to electrically connect the power source 509 to the coils 505, thereby activating the coils 505 and negating the permanent magnet 503 magnetic field to allow free rotation of the x-ray tube head 68; then rotate the x-ray tube head 68 to a desired orientation; then release the control switches 78 to deactivate the electrically conductive coils 505 so that the magnetic field of the permanent magnets 503 pull the metal ring 511 against the friction material 506 to provide a frictional resistance against further rotation of the x-ray tube head 68, thus maintaining the desired rotational orientation of the x-ray tube head 68. The thin friction material 506 may be made from typical materials used for brake pads, such as a ceramic friction material, or a metallic or semi-metallic ceramic mixture including any one or more of iron, copper, steel or graphite bonded together.

Figure 6A:
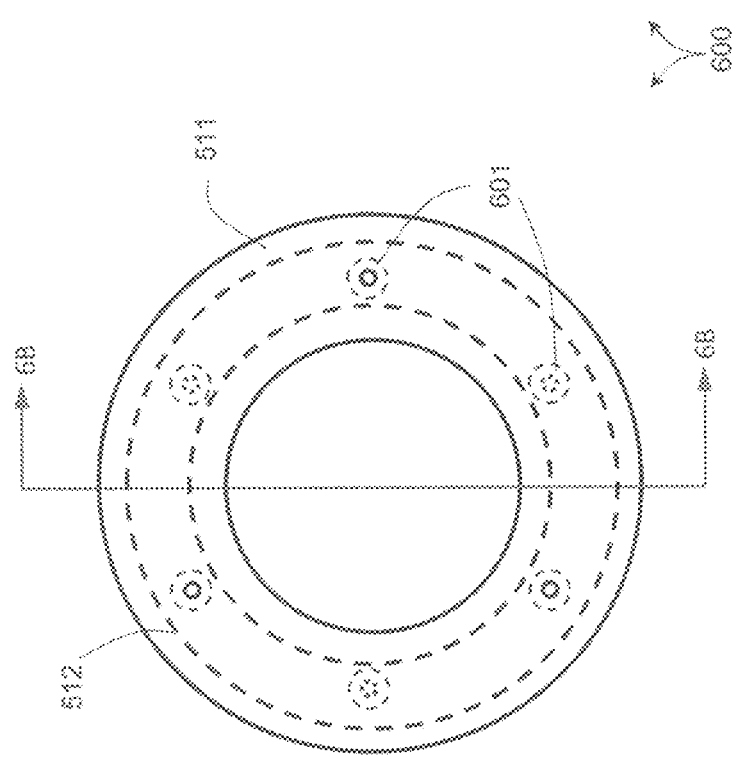
FIGS. 6A-6B illustrate a front view and cross-section side view, respectively, of a flexure plate.
Figure 6B:
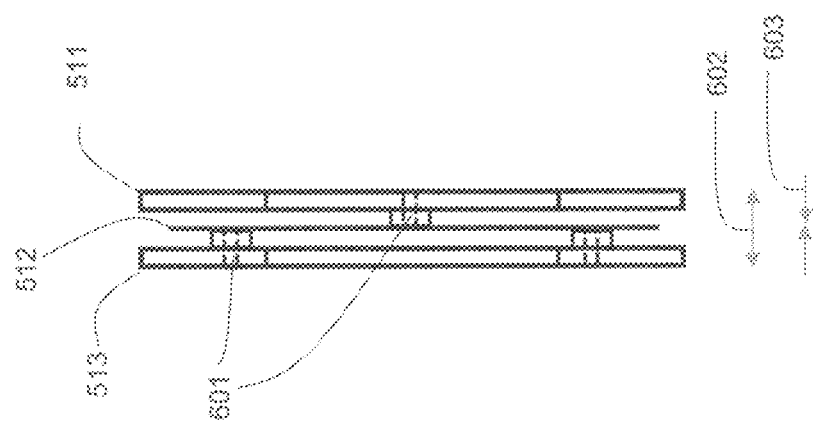

With reference to FIGS. 6A and 6B, there is illustrated a flexure plate 600 having two metal rings 511, 513, and a thin sheet metal ring 512, secured therebetween using three screw+washer combinations 601 for each metal ring 511, 513. The screw+washer combinations 601 are equally spaced on each metal ring 511, 513, positioned about one hundred twenty degrees apart so that each screw+washer combination 601 on one ring 511, 513, is spaced between two adjacent screw+washer combinations 601 on the other ring 513, 511. The flexure plate 600 assumes a resting position such as shown in the cross section side view of FIG. 6B wherein the thin sheet metal ring 512 lies flat in a plane. The flexure plate 600 provides some tensional flexure 602 at any point about its circumference and compressional flexure 603 at any point about its circumference, and is biased to return to its resting position as shown. Compressional and tensional flexure is provided by the thin sheet metal ring 512 which bends and flexes inward and outward, respectively, to some extent between its attachment points at the screw+washer combinations 601. Thus, the flexure plate 600 serves to maintain the mount 508 in a constant generally parallel orientation, but for the flexing of the thin sheet metal ring 512, with respect to the flange portion 507 of the stationary insertion section 516.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
a transport frame having wheels attached thereto for rollably transporting the system;
a vertical column mounted on the transport frame;
a horizontal boom attached to the vertical column at a first end of the horizontal boom; and
an x-ray tube head attached to a second end of the horizontal boom opposite the first end, the x-ray tube head attached to the horizontal boom using a rotation assembly,
wherein the rotation assembly comprises:
a non-rotating portion attached to the horizontal boom, the non-rotating portion including a rotor;
a rotatable shaft attached to the non-rotating portion; and
a mount for attaching a tube head thereto, the mount attached to the rotatable shaft, the mount including a brake pad configured to press against the rotor using a permanent magnet, and an electromagnetic coil configured to counteract the permanent magnet when the electromagnetic coil is activated.

2. The system of claim 1, wherein the horizontal boom comprises a telescoping boom having a plurality of sections that are movable horizontally with respect to each other, the plurality of sections each having different diameters, and wherein the non-rotating portion is attached to the horizontal boom by inserting the non-rotating portion into one of the plurality of sections having a smallest diameter.

3. The system of claim 1, wherein the non-rotating portion is attached to the horizontal boom by inserting the non-rotating portion into the horizontal boom.

4. The system of claim 3, wherein the brake pad is positioned between the permanent magnet and the rotor.

5. The system of claim 1, wherein the electromagnetic coil releases the brake pad from pressing against the rotor when the electromagnetic coil is activated.

6. The system of claim 1, wherein the rotor comprises two metal rings and a thin sheet metal ring therebetween, the two metal rings and the thin sheet metal ring all attached together to prevent relative rotational movement thereof.

7. A radiography system comprising:
an x-ray source; and
an arm mechanically attached to the x-ray source, the arm configured to rotatably support the x-ray source using a rotation assembly, the rotation assembly comprising:
a rotationally stationary rotor in the shape of a ring;
a brake mechanism comprising a brake pad, the brake mechanism configured to rotate along a path on the rotor when the brake mechanism is deactivated and to press the brake pad against the rotor to prevent rotation of the brake mechanism when the brake mechanism is not deactivated.

8. The system of claim 7, wherein the brake mechanism comprises a permanent magnet to press the brake pad against the rotor when the brake mechanism is not deactivated.

9. The system of claim 8, wherein the brake mechanism comprises an electromagnetic coil to deactivate the brake mechanism, and wherein a magnetic field generated by electromagnetic coil counteracts a magnetic field of the permanent magnet when the brake mechanism is deactivated.

10. The system of claim 9, further comprising a power source to power the electromagnetic coil to generate the counteracting magnetic field.

11. The system of claim 10, further comprising a manual switch for connecting the power source to the brake mechanism to power the electromagnetic coil.

12. The brake assembly of claim 11, wherein the permanent magnet comprises neodymium.

* * * * *